United States Patent [19]

Maher et al.

[11] Patent Number: 4,774,361

[45] Date of Patent: Sep. 27, 1988

[54] TRANSITION METAL COMPLEX CATALYZED REACTIONS

[75] Inventors: John M. Maher, Charleston; David R. Bryant, South Charleston, both of W. Va.

[73] Assignee: Union Carbide Corporation, Danbury, Conn.

[21] Appl. No.: 46,821

[22] Filed: May 11, 1987

Related U.S. Application Data

[63] Continuation-in-part of Ser. No. 865,061, May 20, 1986, Pat. No. 4,717,775, which is a continuation-in-part of Ser. No. 685,025, Dec. 28, 1984, Pat. No. 4,599,206, which is a continuation-in-part of Ser. No. 581,352, Feb. 17, 1984, abandoned.

[51] Int. Cl.$^4$ .................. C07C 45/50; C07C 45/82
[52] U.S. Cl. .................. 568/454; 568/492
[58] Field of Search .................. 568/454, 492

[56] References Cited

U.S. PATENT DOCUMENTS

| | | | |
|---|---|---|---|
| 3,871,970 | 3/1975 | Juergen | 568/454 |
| 4,041,082 | 8/1977 | Onoda | 568/454 |
| 4,148,830 | 5/1984 | Pruett et al. | 568/454 |
| 4,235,744 | 11/1980 | Peas et al. | 568/454 |
| 4,419,490 | 12/1983 | Bayer | 525/61 |
| 4,482,748 | 7/1984 | Booth | 568/454 |
| 4,482,749 | 11/1984 | Dennis | 568/454 |
| 4,504,684 | 3/1985 | Fox et al. | 568/454 |
| 4,528,403 | 7/1985 | Tano et al. | 568/454 |
| 4,528,404 | 7/1985 | Oswald et al. | 568/454 |
| 4,567,306 | 1/1986 | Dennis et al. | 568/454 |
| 4,599,206 | 7/1986 | Billig et al. | 568/454 |
| 4,599,456 | 7/1986 | Drake | 568/492 |
| 4,613,701 | 9/1986 | Strong | 568/454 |
| 4,668,651 | 5/1987 | Billig et al. | 502/165 |

FOREIGN PATENT DOCUMENTS

| | | | |
|---|---|---|---|
| 2145532 | 3/1973 | Fed. Rep. of Germany | 568/492 |
| 2326489 | 12/1974 | Fed. Rep. of Germany | 568/492 |
| 0156528 | 9/1982 | Fed. Rep. of Germany | 568/492 |
| 0082714 | 7/1978 | Japan | 568/492 |

OTHER PUBLICATIONS

Dunworth et al., "Advances in Catalysis" vol. 6, pp. 125–141.
Hirai et al., "J. Macromol. Sc. Chem." A12(8), 1117–1141 (1978).
Hirai et al., "J. Macromol. Sc. Chem." A13(6), pp. 727–750 (1979).
Chem. Soc. Japan, Chemistry Letters, pp. 905–910 (1976).
Rampino et al., "J. Amer. Chem. Soc." vol. 63, pp. 2745–2749 (1941).

*Primary Examiner*—Werren B. Lone
*Attorney, Agent, or Firm*—Reynold J. Finnegan

[57] ABSTRACT

The use of an organic polymer additive to minimize or prevent the rhodium of a rhodiumorganophosphite complex catalyst from precipitating from solution during a liquid recycle hydroformylation process.

6 Claims, No Drawings

TRANSITION METAL COMPLEX CATALYZED REACTIONS

This application is a continuation-in-part of U.S. application Ser. No. 865,061 filed May 20, 1986, now U.S. Pat. No. 4,717,775, which is a continuation-in part of U.S. application Ser. No. 685,025 filed Dec. 28, 1984, now U.S. Pat. No. 4,599,206, which is a continuation-in-part of U.S. application, Ser. No. 581,352 filed Feb. 17, 1984, now abandoned.

BRIEF SUMMARY OF THE INVENTION

1. Technical Field

This invention relates to solubilized rhodium phosphite complex catalyzed liquid recycle hydroformylation process.

2. Background Art

It is known in the art that aldehydes may be readily produced by reacting an olefinically unsaturated compound with carbon monoxide and hydrogen in the presence of a solubilized rhodium-phosphite ligand complex catalyst and that a preferred type of such processes involves continuous hydroformylation and recycling of the catalyst, such as disclosed e.g. in U.S. Pat. No. 4,599,206.

However, despite the benefits attendant with such solubilized rhodium-phosphite complex catalyzed liquid recycle hydroformylation processes, under certain circumstances, the rhodium of some rhodium-phosphite complex catalysts may precipitate from solution during such hydroformylation, as rhodium metal or in the form of clusters of rhodium. For instance, observation has indicated that such a rhodium loss phenomenon during a liquid recycle process may be caused by heating the complex catalyst when it is in the absence of combined CO and $H_2$ gas (syn gas) or in contact with lower syn gas concentrations than are normally in contact with the catalyst during the hydroformylation. Such an occasion may occur during liquid recycle hydroformylation operations that involve the recovery of the aldehyde product by distillation from a reaction product solution containing the solubilized rhodium-phosphite complex catalyst and aldehyde product, indicating that it is the distillative aldehyde recovery procedure that is mainly responsible for such rhodium loss, although the exact point of precipitation has not been determined.

DISCLOSURE OF THE INVENTION

It has now been discovered that such rhodium precipitation in solubilized rhodium-phosphite complex catalyzed liquid recycle hydroformylation may be minimized or prevented by carrying out the distillative recovery of the aldehyde product of such a process in the presence of an organic polymer containing polar functional groups wherein said groups are selected from the class consisting of amide, ketone, carbamate, urea and carbonate radicals.

Thus it is an object of this invention to provide an improved solubilized rhodium-phosphite complex catalyzed liquid recycle operation wherein such precipitation of the rhodium of the complex catalyst from solution is minimized or prevented by employing an organic polymer additive containing polar functional groups as disclosed herein. Other objects and advantages of this invention will become readily apparent from the following written description and appended claims.

Accordingly a generic aspect of this invention can be described as a method for minimizing or preventing the precipitation of the rhodium of a rhodium phosphite complex catalyst from solution as rhodium metal or rhodium clusters that may occur during a solubilized rhodium-phosphite complex catalyzed, liquid recycle hydroformylation process for producing aldehyde by reacting an olefinic unsaturated compound with carbon monoxide and hydrogen and which involves the recovery of the aldehyde product by distillation from a reaction product solution containing the solubilized rhodium-phosphite complex catalyst and aldehyde product, said method comprising carrying out said distillation of the aldehyde product from a reaction product solution containing the solubilized rhodium-phosphite complex catalyst, aldehyde product, and in addition an organic polymer containing polar functional groups wherein said groups are selected from the class consisting of amide, ketone, carbamate, urea and carbonate radicals.

DETAILED DESCRIPTION

Accordingly the subject invention encompasses improving the rhodium stability of any solubilized rhodium-phosphite catalyzed, liquid recycle hydroformylation process which may experience such rhodium precipitation from solution, by carrying out the distillative recovery of the aldehyde product from a reaction product solution containing the complex catalyst and aldehyde product in the added presence of an organic polymer containing polar functional groups as defined herein.

Illustrative solubilized rhodium-phosphite complex catalyzed, liquid recycle hydroformylation process in which such rhodium precipitation may occur include such processes as described e.g. in U.S. Pat. Nos. 4,482,749 and 4,599,206 as well as U.S. applications, Ser. Nos. 772,859 and 772,891, both filed Sept. 5, 1985 now U.S. Pat. Nos. 4,668,651 and 4,748,261 respectively and Ser. No. 012,329 filed Feb. 9, 1987, the entire disclosures of which are incorporated herein by reference thereto.

In general such hydroformylation reactions involve the production of aldehydes by reacting an olefinic unsaturated compound with carbon monoxide and hydrogen in the presence of a solubilized rhodium-phosphite complex catalyst in a liquid medium that also contains a solvent for the catalyst, and free phosphite ligand, i.e. ligand that is not complexed with the rhodium metal in the active complex catalyst. The recycle procedure generally involves withdrawing a portion of the liquid reaction medium containing the catalyst and aldehyde product from the hydroformylation reaction zone, either continuously or intermittently, and distilling the aldehyde product therefrom in one or more stages under normal, reduced or elevated pressure, as appropriate, in a separate distillation zone in order to recover the aldehyde product and other volatile materials in vaporous form, the non-volatilized rhodium catalyst containing residue being recycled to the reaction zone. Condensation of the volatilized materials, and separation and recovery thereof, e.g. by distillation, can be carried out in any conventional manner, the aldehyde product being passed on for further purification if desired and any recovered reactants e.g. olefinic starting material and syn gas recycled in any desired manner to the hydroformylation zone. Likewise, the recovered non-volatilized rhodium catalyst containing residue can be recycled with or without further treatment to the hydroformylation zone in any conventional manner desired. Accordingly, the processing techniques of this invention may correspond to any of the known processing techniques heretofore employed in conventional liquid catalyst recycle hydroformylation reactions.

Illustrative rhodium-phosphite complex catalysts employable in such hydroformylation reactions encompassed by this invention may include those disclosed in the above mentioned patents and applications. In general such catalysts may be preformed or formed in situ as described in such references and consist essentially of rhodium in complex combination with an organophosphite ligand. It is believed that carbon monoxide is also present and complexed with the rhodium in the active species. The active catalyst species may also contain hydrogen directly bonded to the rhodium.

Illustrative organophosphite ligands that may be employed as the phosphite ligand complexed to the rhodium catalyst and/or free phosphite ligand in such hydroformylation reactions encompassed by this invention may include a variety of tertiary organophosphites, such as preferably diorganophosphites of the formula

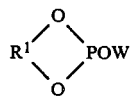

Formula I wherein, $R^1$ represents a divalent organic radical and W represents a substituted or unsubstituted monovalent hydrocarbon radical.

Representative divalent radicals represented by $R^1$ in Formula I above include those wherein $R^1$ may be a divalent acyclic radical or a divalent aromatic radical. Illustrative divalent acyclic radicals are e.g. alkylene, alkylene-oxy-alkylene, alkylene-NX-alkylene wherein is hydrogen or a monovalent hydrocarbon radical, alkylene-S-alkylene, and cycloalkylene radicals; and the like, such as disclosed more fully e.g. in U.S. Pat. Nos. 3,415,906 and 4,567,306, and the like, the entire disclosures of which are incorporated herein by reference thereto. Illustrative divalent aromatic radicals are e.g. arylene, bi-arylene, arylene-alkylene, arylene alkylene-arylene, arylene-oxy-arylene, arylene-oxy-alkylene, arylene-NX-arylene and arylene NX-alkylene wherein X is hydrogen or a monovalent hydrocarbon radical, arylene-S-alkylene, and arylene-S-arylene radicals; and the like. More preferably $R^1$ is a divalent aromatic radical.

Representative of a more preferred class of tertiary diorganophosphites are diorganophosphites of the formula

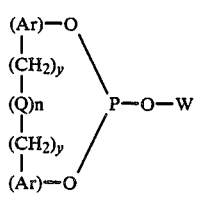

Formula II wherein W is a substituted or unsubstituted monovalent hydrocarbon radical, Ar is a substituted or unsubstituted aryl radical, each Ar being the same or different, each y individually has a value of 0 or 1, Q is a divalent bridging group selected from the group consisting of $-CR^3R^4-$, $-O-$, $-S-$, $-NR^5-$, $SiR^6R^7-$ and $-CO-$, wherein each $R^3$ and $R^4$ is independently selected from the group consisting of hydrogen, alkyl radicals having 1 to 12 carbon atoms, phenyl, tolyl and anisyl, wherein each $R^5$, $R^6$ and $R^7$ are independently hydrogen or a methyl radical, and n has a value of 0 or 1. Formula II type diorganophosphites are described in greater detail, e.g., in U.S. Pat. No. 4,599,206 and U.S. application Ser. No. 865,061 filed May 20, 1986, the entire disclosures of which are incorporated herein by reference thereto.

Among the more preferred diorganophosphites are those of the formula

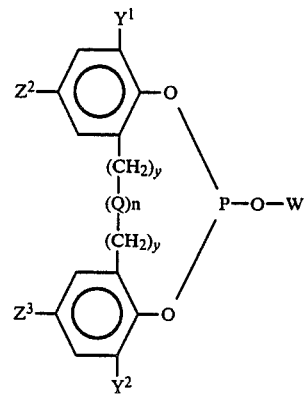

FORMULA III wherein Q is $-CR^1R^2$ and each $R^1$ and $R^2$ radical individually represents a radical selected from the group consisting of hydrogen and alkyl; wherein each y individually has a value of 0 or 1, and n has a value of 0 to 1; wherein W represents in unsubstituted or substituted monovalent hydrocarbon radical selected from the group consisting of alkyl radicals having from 1 to 18 carbon atoms, (such as primary, secondary and tertiary alkyl radicals e.g. methyl, ethyl, n-propyl, isopropyl, butyl, sec-butyl, t-butyl, t-butylethyl, t butylpropyl, n-hexyl, amyl, sec-amyl, t-amyl, iso-octyl, 2-ethylhexyl, decyl, octadecyl, and the like) as well as, aryl radicals, such as alpha-naphthyl, beta-naphthyl, and aryl radicals of the formula

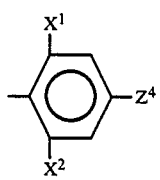

and wherein each $X^1$, $X^2$, $Y^1$, $Y^2$, $Z^2$, $Z^3$, and $Z^4$ group individually represents a radical selected from the group consisting of hydrogen, an alkyl radical having from 1 to 8 carbon atoms, substituted or unsubstituted aryl, alkaryl, aralkyl and alicyclic radicals (e.g. phenyl, benzyl, cyclohexyl, 1-methylcyclohexyl, and the like), hydroxy (—OH), and an ether (i.e oxy) radical such as —$OR^8$ wherein $R^8$ is an alkyl radical of 1 to 18 carbon atoms. Among the even more preferred diorganophosphites are those of Formula III above as described in the claims of U.S. Pat. No. 4,599,206 and disclosed in U.S. patent application, Ser. No. 685,061, filed May 20, 1986.

Illustrative diorganophosphites include e.g. those of the following formulas wherein t-Bu is a tertiary butyl radical; and Me is a methyl radical.

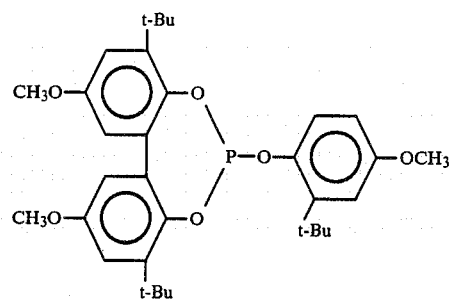
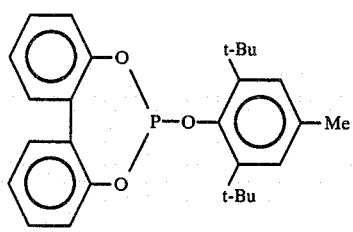
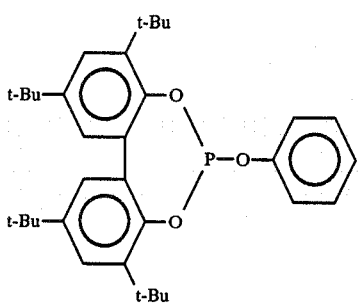
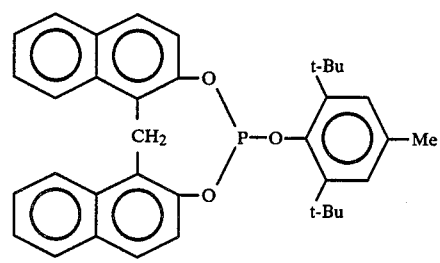
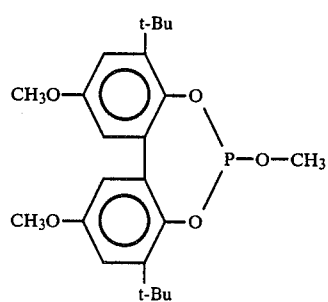
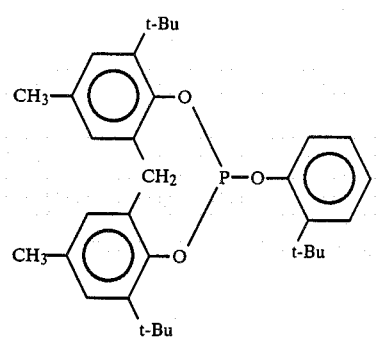
-continued
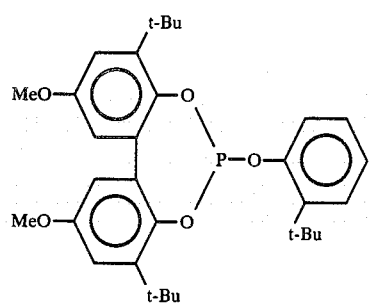
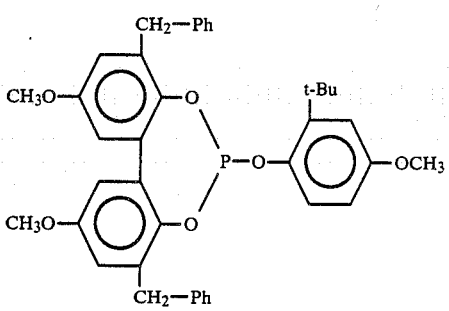
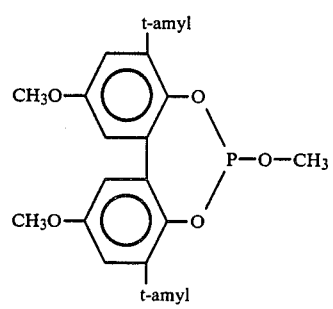
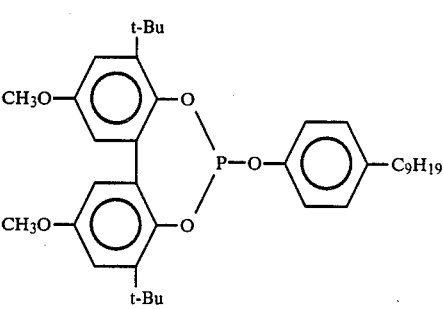

-continued

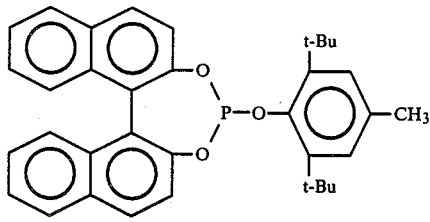

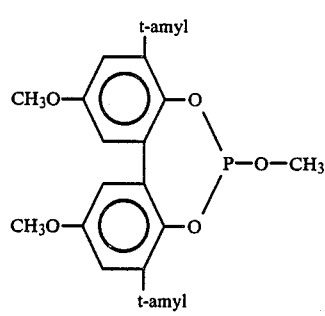

and the like.

Still another group of tertiary organophosphites that may be employed in such hydroformylation reactions encompassed by this invention are tertiary organopolyphosphites. Such phosphites may contain two or more of such tertiary (trivalent) phosphorus atoms such as those of the formula

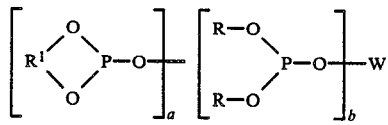

Formula IV wherein W represents a substituted or unsubstituted m-valent hydrocarbon radical, wherein $R^1$ is the same as defined in Formula I above, wherein each R is independently a substituted or unsubstituted monovalent hydrocarbon radical, wherein a and b can each have a value of 0 to 6 with the proviso that the sum of a +b is 2 to 6 and m equals a +b. Illustrative tertiary organopolyphosphites may include bisphosphites such as those of the formulas

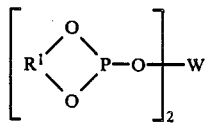

Formula V wherein $R^1$ is a divalent organic radical as defined in Formula I above and wherein W is a substituted or unsubstituted divalent hydrocarbon radical; and

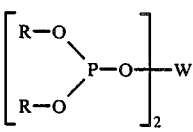

Formula VI wherein each R is independently a substituted or unsubstituted monovalent hydrocarbon radical, and wherein W is a substituted or unsubstituted divalent hydrocarbon radical; and

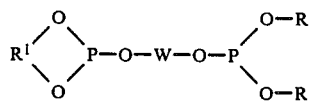

Formula VII wherein $R^1$ is a divalent organic radical as defined in Formula I above, wherein each R is independently a substituted or unsubstituted monovalent hydrocarbon radical, and wherein W is a substituted or unsubstituted divalent hydrocarbon radical.

Representative of another class of tertiary organobisphosphites that may be used in such hydroformylation reactions encompassed by this invention are bisphosphites of the formula

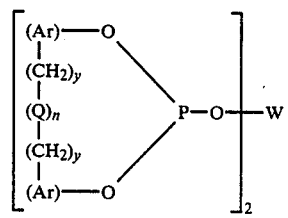

Formula VIII wherein each Ar group represents an identical or different, substituted or unsubstituted aryl radical; wherein W represents a divalent radical selected from th group consisting of alkylene, alkylene oxy alkylene, arylene and arylene(CH$_2$)y—(Q)n-(CH$_2$)y-arylene, wherein each arylene radical is the same as Ar defined above; wherein each Q individually represents a divalent bridging group selected from the class consisting of —CR$^3$R$^4$—, —O—, —S—, —NR$^5$, —SiR$^6$R$^7$ and —CO—, wherein each R$^3$ and R$^4$ radical individually represents a radical selected from the group consisting of hydrogen and alkyl, wherein each R$^5$, R$^6$, and R$^7$ radical individually represents —H or —CH$_3$; wherein each y and n individually has a value of 0 or 1. Formula VIII type bisphosphites are described in greater detail e.g., in U.S. Pat. Nos. 4,351,759 and U.S. patent applications, Ser. Nos. 772,859 and 12329 filed Sept. 5, 1985 and Feb. 9, 1987, the entire disclosures of which are incorporated herein by reference thereto.

Representative of yet another class of tertiary organobisphosphites that may be employed in such hydroformylation reactions encompassed by this invention are bisphosphites of the formula

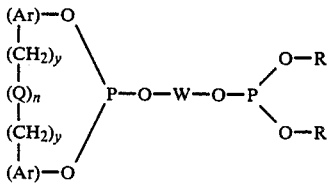

Formula IX wherein each Ar group represents an identical or different, substituted or unsubstituted aryl radical; wherein W represents a divalent radical selected from the group consisting of alkylene, arylene and arylene —(CH$_2$)y—(Q)n-(CH$_2$)y-arylene-, wherein each arylene radical is the same as Ar defined above; wherein each Q individually represents a divalent bridging group selected from the class consisting of —CR³R⁴—, —O—, —S—, —NR⁵—, —SiR⁶R⁷— and —CO—, wherein each R³ and R⁴ radical individually represents a radical selected from the group consisting of hydrogen. and alkyl, wherein each R⁵, R⁶, and R⁷ radical individually represents —H or —CH₃; wherein each y and n individually has a value of 0 or 1; and wherein each R group individually represents a radical selected from the group consisting of substituted or unsubstituted monovalent hydrocarbon radicals such as alkyl, aryl, alkaryl, aralkyl and alicyclic radicals. Formula IX type bisphosphites are described in greater detail e.g., in U.S. Pat. application, Ser. No. 772,891 filed Sept. 5, 1985, the entire disclosure of which is incorporated herein by reference thereto.

Another group of tertiary organophosphites that may be employed in such hydroformylation reactions encompassed by this invention are tertiary mono organophosphites of the formula

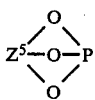

Formula X wherein Z⁵ represents a trivalent organic radical, such as described in greater detail e.g. in U.S. Pat. No. 4,567,306, the entire disclosure of which is incorporated herein by reference thereto.

Finally another group of tertiary organophosphites that may be employed in such hydroformylation reactions encompassed by this invention include triorganophosphites, such as tris(ortho-phenyl)phenyl phosphite, tris(ortho-methyl)phenyl phosphite, tris(ortho-t-butyl)phenyl phosphite, and the like.

Thus the phosphite ligand employable in the hydroformylation reactions encompassed by this invention as the phosphite ligand of the rhodium-phosphite complex catalyst and/or as the free phosphite ligand present in the hydroformylation reaction medium and liquid solutions throughout the hydroformylation process may be a tertiary organic phosphite ligand selected from the group consisting of mono organophosphites, diorganophosphites, triorganophosphites, and organopolyphosphites, such as described above.

The hydroformylation process encompassed by this invention may be carried out in any excess amount of free phosphite ligand desired, e.g. at least one mole of free phosphite ligand per mole rhodium present in the reaction medium on up to 100 moles of free phosphite ligand or higher if desired. In general amounts of organophosphite ligand of from about 4 to about 50 moles per mole rhodium present in the reaction medium should be suitable for most purposes, said amounts being the sum of both the amount of phosphite that is bound (complexed) to the rhodium present and the amount of free (non-complexed) phosphite ligand present. Of course, if desired, make-up phosphite ligand can be supplied to the reaction medium of the hydroformylation process, at any time and in any suitable manner, to maintain a predetermined level of free ligand in the reaction medium. Moreover, it is to be understood that while the phosphite ligand of the rhodium-phosphite complex catalyst and excess free phosphite ligand in a given process are both normally the same, different phosphite ligands, as well as, mixtures of two or more different phosphite ligands may be employed for each purpose in any given process, if desired.

The amount of rhodium-phosphite complex catalyst present in the reaction medium of a given hydroformylation process encompassed by this invention need only be that minimum amount necessary to provide the given rhodium concentration desired to be employed and which will furnish the basis for at least that catalytic amount of rhodium necessary to catalyze the particular hydroformylation process involved such as disclosed e.g. in the above-mentioned patents and applications. In general, rhodium concentrations in the range of from about 10 ppm to about 1000 ppm, calculated as free rhodium, in the hydroformylation reaction medium should be sufficient for most processes, while it is generally preferred to employ from about 10 to 500 ppm of rhodium and more preferably from 25 to 350 ppm to rhodium.

The olefinic starting material reactants that may be employed in the hydroformylation reactions encompassed by of this invention can be terminally or internally unsaturated and be of straight-chain, branched-chain or cyclic structure, such as disclosed e.g. in the above-mentioned patents and applications. Such olefins can contain from 2 to 20 carbon atoms and may contain one or more ethylenic unsaturated groups. Moreover, such olefins may contain groups or substituents which do not essentially adversely interfere with the hydroformylation process such as carbonyl, carbonyloxy, oxy, hydroxy, oxycarbonyl, halogen, alkoxy, aryl, alkyl, haloalkyl, and the like. Illustrative olefinic unsaturated compounds include alpha olefins, internal olefins, alkyl alkenoates, alkenyl alkanoates, alkenyl alkyl ethers, alkenols, and the like, e.g. ethylene, propylene, 1-butene, 1-pentene, 1-hexene, 1-octene, 1-decene, 1,-dodecene, 1-octadecene, 2-butene, isobutylene, 2-methylbutene, 2-hexene, 3-hexene, 2-heptene, cyclohexene, propylene dimers, propylene trimers, propylene tetramers, 2-ethyl-1-hexene, styrene, 3-phenyl-1-propene, 1,4-hexadiene, 1,7-octadiene, 3-cyclohexyl-1-butene, allyl alcohol, hex-1-en-4-ol, oct-1-en-4-ol, vinyl acetate, allyl acetate, 3-butenyl acetate, vinyl propionate, allyl propionate, allyl butyrate, methyl methacrylate, 3-butenyl acetate, vinyl ethyl ether, vinyl methyl ether, allyl ethyl ether, n-propyl-7-octenoate, 3-butenenitrile, 5-hexenamide, and the like. Of course, it is understood that mixtures of different olefinic starting materials can be employed, if desired. More preferably the olefinic unsaturated starting materials are alpha olefins containing from 2 to 20 carbon atoms, and internal olefins containing from 4 to 20 carbon atoms as well as starting material mixtures of such alpha olefins and internal olefins.

As noted above hydroformylation reactions encompassed by this invention are also conducted in the presence of an organic solvent for the rhodium-phosphite complex catalyst. Any suitable solvent which does not unduly adversely interfere with the intended hydroformylation process can be employed. Illustrative suitable solvents for rhodium catalyzed hydroformylation processes include those disclosed e.g. in the above mentioned patents and applications. Of course mixtures of one or more different solvents may be employed if desired. Most preferably the solvent will be one in which the olefinic starting material, hydroformylation catalyst and organic polymer additive employed herein are all substantially soluble. In general, it is preferred to employ aldehyde compounds corresponding to the aldehyde products desired to be produced and/or higher boiling aldehyde liquid condensation by products as the primary solvent such as the higher boiling aldehyde liquid condensation by-products that are produced in situ during the hydroformylation process. Indeed, while one may employ any suitable solvent at the start up of a continuous process, the primary solvent will normally eventually comprise both aldehyde products and higher boiling aldehyde liquid condensation by products due to the nature of such continuous processes. Such aldehyde condensation by-products can also be preformed if desired and used accordingly. Of course, the amount of solvent employed is not critical to the subject invention and need only be that amount sufficient to provide the reaction medium with the particular rhodium concentration desired for a given process. In general, the amount of solvent when employed may range from about 5 percent by weight up to about 95 percent by weight or more based on the total weight of the reaction medium.

Thy hydroformylation reaction conditions that may be employed in the hydroformylation processes encompassed by this invention may include any suitable continuous liquid catalyst recycle hydroformylation conditions heretofore disclosed in the above-mentioned patents and applications. For instance, the total gas pressure of hydrogen, carbon monoxide and olefinic unsaturated starting compound of the hydroformylation process may range from about 1 to about 10,000 psia. In general, however, it is preferred that the process be operated at a total gas pressure of hydrogen, carbon monoxide and olefinic unsaturated starting compound of less than about 1500 psia. and more preferably less than about 500 psia. The minimum total pressure being limited predominately by the amount of reactants necessary to obtain a desired rate of reaction. More specifically the carbon monoxide partial pressure of the hydroformylation process of this invention is preferably from about 1 to about 120 psia. and more preferably from about 3 to about 90 psia, while the hydrogen partial pressure is preferably about 15 to about 160 psia and more preferably from about 30 to about 100 psia. In general $H_2$: CO molar ratio of gaseous hydrogen to carbon monoxide may range from about 1:10 to 100:1 or higher, the more preferred hydrogen to carbon monoxide molar ratio being from about 1:1 to about 10:1. Further, the hydroformylation process may be conducted at a reaction temperature from about 45° C. to about 150° C. In general, hydroformylations at reaction temperatures of about 50° C. to about 120° C. are preferred for all types of olefinic starting materials, since no substantial benefit is seem in operating at reaction temperatures much above 120° C. and such is considered to be less desirable, due to possible catalyst activity decline as disclosed e.g. in U.S. Pat. No. 4,599,206.

Moreover as noted herein, the solubilized rhodium-phosphite complex catalyzed continuous hydroformylation process employable in this invention involves a liquid catalyst recycle procedure. Such types of liquid catalyst recycle procedures are known as seen disclosed e.g. in the above-mentioned patents and applications, and thus need not be particularly detailed herein, since any such conventional catalyst recycle procedures may be employed by this invention. For instance in such liquid catalyst recycle procedures it is common place to continuously remove a portion of the liquid reaction product medium, containing e.g. the aldehyde product, the solubilized rhodium-phosphite complex catalyst, free phosphite ligand, and organic solvent, as well as by-products produced in situ by the hydroformylation, e.g. aldehyde condensation by-products etc., and unreacted olefinic starting material, carbon monoxide and hydrogen (syn gas) dissolved in said medium, from the hydroformylation reactor, to a distillation zone, e.g. a vaporizer/separator wherein the desired aldehyde product is distilled in one or more stages under normal, reduced or elevated pressure as appropriate and separated from the liquid medium. The vaporized or distilled desired aldehyde product so separated may then be condensed and recovered in any conventional manner as discussed above. The remaining non-volatilized liquid residue which contains rhodium- phosphite complex catalyst, solvent, free phosphite ligand and usually some undistilled aldehyde product is then recycled back, with or without further treatment as desired, along with whatever by-product and non-volatilized gaseous reactants that might still also be dissolved in said recycled liquid residue, in any conventional manner desired, to the hydroformylation reactor, such as disclosed e.g. in the above-mentioned patents and applications. Moreover the reactant gases so removed by such distillation from the vaporizer may also be recycled back to the reactor if desired.

The distillation and separation of the desired aldehyde product from the rhodium-phosphite complex catalyst containing product solution may take place at any suitable temperature desired. In general it is recommended that such distillation take place at low temperatures, such as below 150° C., preferably below 140° C., and more preferably at a temperature in the range of from about 50° C. to about 130° C. It is also generally recommended that such aldehyde distillation take place under reduced pressure, e.g. a total gas pressure that is substantially lower than the total gas pressure employed during hydroformylation when low boiling aldehydes (e.g. $C_4$ to $C_6$) are involved or under vacuum when high boiling aldehydes (e.g. $C_7$ or greater) are involved. For instance, a common practice is to subject the liquid reaction product medium removed from the hydroformylation reactor to a pressure reduction so as to volatilize a substantial portion of the unreacted gases dissolved in the liquid medium and then pass said volatilized gases and liquid medium which now contains a much lower syn gas concentration than was present in the hydroformylation reaction medium to the distillation zone e.g. vaporizer/separator, wherein the desired aldehyde product is distilled. In general distillation pressures ranging from vacuum pressures or below on up to total gas pressures of about 50 psig should be sufficient for most purposes.

As stated above, the subject invention resides in the discovery that the possibility of rhodium precipitation as discussed herein can be minimized or prevented by carrying out such distillation of the desired aldehyde product from such rhodium-phosphite catalyst containing product solutions in the added presence of an organic polymer containing polar functional groups wherein said functional groups are selected from the class consisting of amide (i.e. any

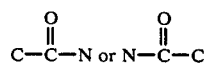

group regardless of further substitution), ketone i.e. any

group regardless of further substition), carbamates (i.e

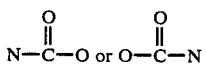

groups regardless of further substitution), urea (i.e, any

group regardless of further substitution) and carbonate (i.e.

group regardless of further substitution) radicals.

The organic polymer additives which are employable herein and are added to the rhodium catalyst containing product solution from which the desired aldehyde product is distilled are well known compounds as are methods for their preparation and in general are readily commercially available. Any organic polymer, including homopolymers, copolymers, terpolymers and oligomers containing such polar functional groups may be employed herein. Moreover, it is to be understood that such polar functional groups may be present in the organic polymers as radical substituents stemming off the backbone of the polymer and/or as radicals that are incorporated in and form part of the backbone of the polymer. Further, said polar functional groups may be of a non-cyclic nature or part of a cyclic radical. It is to be further understood that the organic polymers may contain only one type of such polar functional groups or two or more different types of such polar functional groups. Illustrative organic polymers containing such polar functional groups that are employable in this invention include e.g. polyvinylpyrollidone, vinylpyrrolidone-vinyl acetate copolymers, polyacrylamides, copolymers of vinylpyrrolidone and beta-dimethylaminoethyl methacrylate, carbamic acid, N-[polymethylene(polyphenyl)]methylester, N [polymethylene (polyphenyl)]N′-diisopropyl urea, copolymers of vinyl pyrrolidone and long chain alpha olefins, copolymers of vinyl pyrrolidone and styrene, polyacrylic acid hydrazide, poly-N-vinyl-5-methoxazolidone, polypeptides, e.g. poly-L-pyroline and poly-L-phenylalanine, and the like. The average molecular weight of such organic polymers does not appear to be narrowly critical and may range from about 400 up to 10,000,000 or higher, nor does the amount of such polar functional groups on the polymer appear narrowly critical. The preferred organic polymers employable as additives in this invention are those containing at least three such polar functional groups, especially functional amide groups, and more preferably vinylpyrrolidone polymers and copolymers. Vinylpyrrolidone-vinyl acetate copolymers because of their general superior solubility in the rhodium-phosphite containing hydroformylation solutions are most preferred.

Moreover the amount of such organic polymer additives employable in any given process of this invention need only be that minimum amount necessary to furnish the basis for at least some minimization of such rhodium loss that might be found to occur as a result of carrying out an identical rhodium catalyzed liquid recycle hydroformylation process under identical conditions, save for carrying out said identical process in the absence of the identical organic polymer employed in said given process. Amounts of such organic polymer additives ranging from about 0.01 up to about 10 weight percent, or higher if desired, based on the total weight of the hydroformylation reaction product solution to be distilled should be sufficient for most purposes. It is of course to be understood that as the aldehyde product is distilled from the hydroformylation product solution the concentration of the non-volatilized components therein, e.g. catalyst and organic polymer additive, will increase accordingly. Thus the upper amount of organic polymer additive employable herein is governed primarily only by the solubility limit of the organic polymer in the non-volatilized liquid rhodium catalyst containing residue obtained after distillation removal of as much of the aldehyde product desired. Such amounts of organic polymer additive employable herein will of course depend in part on the particular rhodium catalyst employed and the desired distillation temperature for recovering the aldehyde product as well as the particular organic polymer additive itself. In general it is preferred to employ amounts of such organic polymer additives in the range of about 0.1 to about 5.0 and more preferably from about 0.3 to about 3.0 weight percent based on the total weight of the hydroformylation reacion product to be distilled.

The ability to employ such low amounts of the organic polymer additive useful herein to minimize or prevent such rhodium precipitation from solution is another important beneficial aspect of this invention in that such small amounts of additives are far less likely to unduly adversely affect the composition of the rhodium catalyst and/or hydroformylation process as might occur with large amounts of additives. For example, the presence of small amounts of polyvinylpyrrolidone and vinylpyrrolidone-vinyl acetate copolymer in the hydroformylation medium of certain hydroformylation experiments involving continuous rhodium-phosphite complex catalyzed hydroformylation of butene-2 without any catalyst recycle were observed not to substantially affect either the rate of reaction or the aldehyde product isomer ratio obtainable in the absence of such polymer additives. In another such experiment involving the continuous hydroformylation of isobutylene without catalyst recycle, the rate of reaction was accelerated by the presence of polyvinylpyrrolidone; while in yet another such experiment involving the hydroformylation of butene-2 without catalyst recycle and employing Ligand A as herein defined below, the addition of a vinyl pyrrolidone vinyl acetate copolymer was observed to improve ligand stability. Moreover, the organic polymer additives employable in this invention are highly non volatile and thus do not pose contamination problems in product refining of the desired aldehyde.

The addition of the organic polymer additives employable in this invention to the reaction product solution from which the aldehyde product is to be distilled may be carried out in any suitable manner desired. For instance, the organic polymer additive may be added to the reaction product solution that has been removed from the reactor and at any time prior to or during the distillation of the aldehyde product therefrom, and may also be removed if desired from the non-volatilized liquid rhodium catalyst containing residue obtained after distillation of as much of the aldehyde product desired, e.g., prior to or during the recycling of said non-volatilized liquid rhodium catalyst containing residue so as to maintain the hydroformylation reaction medium present in the hydroformylation reactor free of such organic polymer additives. However, since it is not believed that such organic polymer additives will normally have any substantial detrimental affect on the hydroformylation reaction per se, in general it is preferred to added such organic polymer additives directly to the hydroformylation reaction medium and allow the organic polymer additive to remain in solution throughout the entire liquid catalyst recycle hydroformylation solution. Indeed if one has reason to believe that such rhodium precipitation as discussed herein will undoubtedly occur during the desired liquid catalyst recycle hydroformylation process it may be desireable to add the organic polymer to the precursor catalyst solution to be employed so that such organic polymer additives are present right from the start of the hydroformylation process.

Of course it is to be understood that while the optimization of the subject invention necessary to achieve the best results and efficiency desired are dependent upon one's experience in the utilization of the subject invention, only a certain measure of experimentation should be necessary to ascertain those conditions which are optimum for a given situation and such should be well within the knowledge of one skilled in the art and easily obtainable by following the more preferred aspects of this invention as explained herein and/or by simple routine experimentation.

Finally applicants have devised an accelerated testing procedure for demonstrating the potential effectiveness of organic polymer additives for minimizing or preventing such rhodium loss due to the precipitation of rhodium from solution as discussed herein that may occur during a continuous liquid recycle hydrofromylation involving the use of a rhodium-phosphite complex catalyst and distillative recovery of the desired aldehyde product. Said testing procedure is outlined in some of the following Examples and comprises subjecting a solubilized activated rhodium-phosphite complex catalyst solution to much harsher conditions than would be experienced during the distillative recovery of aldehyde product during continuous liquid recycle hydroformylation, in order to obtain meaningful results in a much shorter and manageable period of time. For instance such rhodium loss may take days to define quantitatively under normal aldehyde distillative recovery procedures because such rhodium loss rates are normally no more than a few percent per day, whereas applicants accelerated rhodium loss test can be completed within hours by continously maintaining the catalyst solution at aldehyde recovery type distillation temperatures for a prolonged period of time in the absence of the combined presence of carbon monoxide and hydrogen (syn gas). Further it is to be understood that those test experiments conducted at higher temperatures and/or those which employed rhodium black (which has been observed to promote rhodium precipitation) are considered to be the even harsher tests than the other experiments.

The following examples are illustrative of the present invention and are not to be regarded as limitative.

Moreover as reported in the examples the following designations and conditions are used.

Texanol ®—2,2,4-trimethyl-1,3-pentandeiol monoisobutyrate t-Bu—tertiary butyl radical Me—methyl radical Ligand A—An organophosphite of the formula:

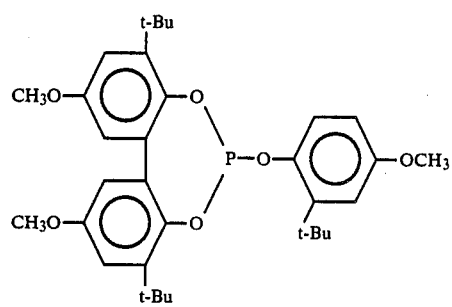

Liquid B—An organophosphite of the formula:

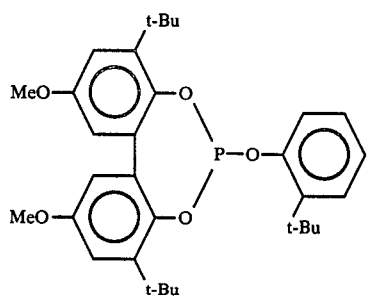

Liquid C—An organophosphite of the formula:

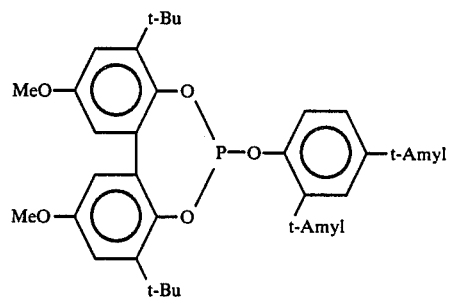

Liquid D—An organophosphite of the formula:

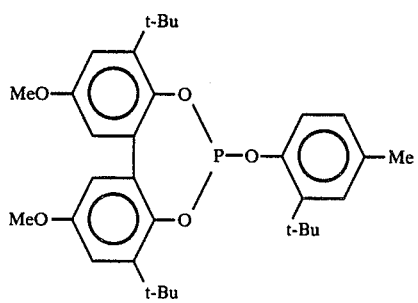

Liquid E—An organophosphite of the formula:

Ligand F—An organophosphite of the formula:

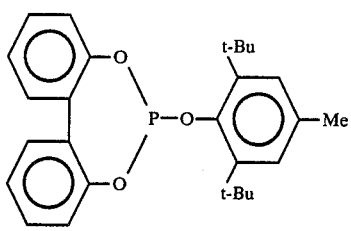

Ligand G—An organophosphite of the formula:

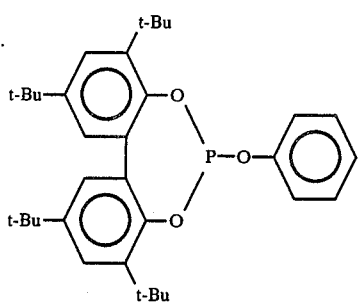

Ligand H—An organophosphite of the formula:

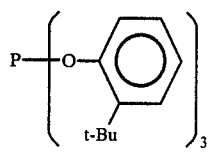

Ligand I—An organophosphite of the formula:

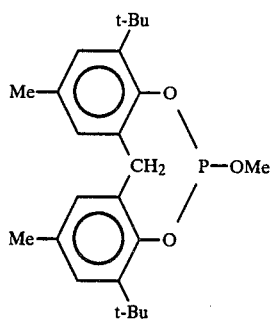

Ligand J—An organophosphite of the formula:

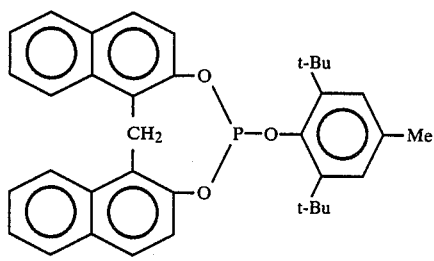

Ligand K—An organophosphite of the formula:

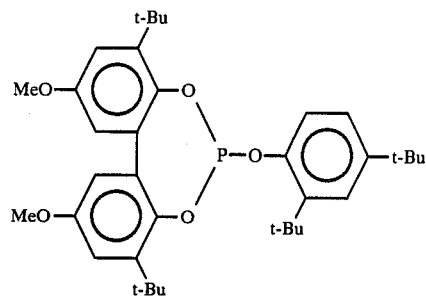

Ligand L—An organophosphite of the formula:

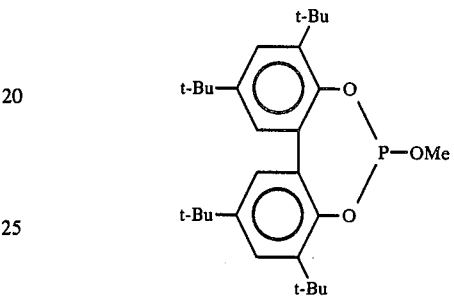

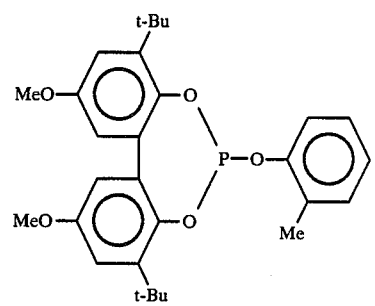

% Rhodum Lost=Amount of rhodium found in the filtered solution divided by the amount of rhodium in the starting solution times 100.

EXAMPLE 1

In each experiment, about 20 ml. of a metal complex catalyst precursor solution containing a phosphite ligand as indicated and 250 ppm rodium as $Rh_4(CO)_{12}$ dissolved in Texanol ® solvent was charged under nitrogen to a nitrogen-flushed three ounce glass aerosol bottle equipped with a magnetic stirring bar. Rhodium black was then added if employed. A nitrogen-flushed gas manifold was attached to the bottle and the system charged to 60 psig with syn gas ($CO/H_2$, 1:1 mole ratio) and vented five times before a final charging with 60 psig. $CO/H_2$. The bottle was placed in an oil bath at the indicated temperature and stirred for one hour to activate the catalyst, whereupon the $CO/H_2$ was vented and the flask charged to 10 psig. with hydrogen or 60 psig. nitrogen gas, as indicated and vented five times. After a final charge of 10 psig. $H_2$ or 60 psig. nitrogen gas, as indicated, the flask was stirred for about 20 hours at the indicated temperature, whereupon a sample was withdrawn by pressure syringe and filtered through a Millipore ® five micron type LS filter (Waters Corp.)

and analyzed for rhodium content by atomic absorption spectroscopy. The results are shown in the following table.

TABLE 1

| Run Nos. | Ligand | Ligand/ Rhodium[a] | Temp. °C. | Rhodium Black[b] | Gas | % Rhodium Lost |
|---|---|---|---|---|---|---|
| 1 | A | 10 | 120 | Yes | $H_2$ | 91.7 |
| 2 | A | 10 | 120 | No | $H_2$ | 70 |
| 3 | B | 10 | 120 | No | $H_2$ | 70 |
| 4 | C | 10 | 120 | No | $H_2$ | 60 |
| 5 | J | 10 | 120 | No | $H_2$ | 64 |
| 6 | D | 10 | 120 | No | $H_2$ | 77 |
| 7 | E | 15 | 130 | Yes | $N_2$ | 96 |
| 8 | E | 10 | 130 | No | $N_2$ | 41 |
| 9 | F | 10 | 130 | No | $N_2$ | 63 |
| 10 | F | 10 | 130 | Yes | $N_2$ | 69 |
| 11 | G | 10 | 130 | Yes | $N_2$ | 84 |
| 12 | H | 10 | 130 | Yes | $N_2$ | 94 |
| 13 | I | 10 | 130 | Yes | $N_2$ | 89 |

[a] Mole equivalents of ligand per mole rhodium
[b] 50 mg Rhodium Black when used The above experiments demonstrate that a large amount of the rhodium precipitated from the solution at 120° C. and 130° C.

EXAMPLE 2

In each experiment, about 20 ml. of a metal complex catalyst precursor solution containing about 10 mole equivalents per mole of rhodium of phosphite ligand referred to herein as Ligand E and 250 ppm rhodium as $Rh_4(CO)_{12}$ dissolved in Texanol ® solvent was charged under nitrogen to a nitrogen-flushed three ounce glass aerosol bottle equipped with a magnetic stirring bar. 50 mg. of rhodium black and an organic polymer as indicated were then added. A nitrogen-flushed gas manifold was attached to the bottle and the system charged to 60 psig with syn gas ($CO/H_2$, 1:1 mole ratio) and vented five times before a final charging with 60 psig. $CO/H_2$. The bottle was placed in an oil bath at 130° C. and stirred for one hour to activate the catalyst, whereupon the $CO/H_2$ was vented and the flask charged to 60 psig. with nitrogen gas and vented five times. After a final charge of 60 psig. nitrogen, the flask was stirred for about 20 hours at 130° C., whereupon a sample was withdrawn by pressure syringe and filtered through a Millipore ® five micron type LS filter (Waters Corp.) and analyzed for rhodium content by atomic absorption spectroscopy. The results are shown in the following table.

TABLE 2

| Run Nos. | Ligand | Organic Polymer Additive (Avg. Mol Wt.) | Wt. % Organic Polymer Used | % Rhodium Lost |
|---|---|---|---|---|
| 1 | E | PMVK | 1.0 | 0 |
| 2 | E | PVP (40,000) | 0.1 | 0 |
| 3 | E | PVP (40,000) | 0.25 | 0 |
| 4 | E | PVP (40,000) | 0.5 | 0 |
| 5 | E | PVP (40,000) | 1.0 | 0 |
| 6 | E | PVP (10,000) | 1.0 | 0 |
| 7 | E | PVPVA (30% vinylpyrrolidone) | 1.0 | 13 |
| 8 | E | PVPVA (50% vinylpyrrolidone) | 1.0 | 0 |
| 9 | E | PVPVA (60% vinylpyrrolidone) | 0.5 | 0 |
| 10 | E | PVPVA (70% vinylpyrrolidone) | 1.0 | 0 |
| 11 | E | PAA (5,000,000–6,000,000) | 1.0 | 0 |
| 12 | E | GAFQUAT ® 755 (1,000,000) | 1.0 | 0 |
| 13 | E | GAFQUAT ® 734 (100,000) | 1.0 | 0 |
| 14 | E | GANEX ® V220 (8600) | 1.0 | 99 |
| 15 | E | GANEX ® V220 (8600) | 5.0 | 33 |
| 16 | E | GANEX ® V216 (7300) | 1.0 | 21 |
| 17 | E | PM(PP)MC (400) | 1.0 | 0 |
| 18 | E | PM(PP)DMU (470) | 1.0 | 5 |
| 19 | E | POLECTRON ® 430 | 1.0 | 0 |
| 20 | E | PLP (1000–10,000) | 0.5 | 0 |
| 21 | E | PLPA (2,000–5,000) | 0.5 | 0 |
| 23 | E | NCHP | 0.5 | 94 |

| | |
|---|---|
| PMVK = | polymethylvinyl ketone (sold by Aldrich Chem. Co.) |
| PVP = | polyvinylpyrrolidone (Run Nos. 2–5, Special Grade sold by Aldrich Chem. Co., Run No. 6, PVP K-15 sold by GAF Corp.) |
| PVPVA = | vinylpyrrolidone-vinyl acetate copolymer (Run No. 7, E-335; Run No. 8, I-535, Run No. 9, S-630, Run No. 10, E-735, all sold by GAF Corp.) |
| PAA = | polyacrylamide (sold by Aldrich Chem. Co.) |
| GAFQUAT ® 755 = | copolymer of vinyl pyrrolidone and beta-dimethylaminoethyl methacrylate (GAF Corp.) |
| PM(PP)MC = | carbamic acid, N—[polymethylene (polyphenyl)] - methylester |
| PM(PP)DMU = | N—[polymethylene (polyphenyl)] N'—diisopropyl urea |
| NCHP = | N—cyclohexyl pyrrolidone monomer |
| GAFQUAT ® 734 = | copolymer of vinylpyrrolidone and beta-dimethylaminoethyl methacrylate, 20% in $H_2O$ (sold by GAF Corp.) |
| GANEX ® V220 = | copolymer of vinylpyrrolidone and long chain alpha olefin (sold by GAF Corp.) |
| GANEX ® V216 = | copolymer of vinylpyrrolidone and long chain alpha olefin (sold by GAF Corp.) |
| Polectron ® 430 = | copolymer of vinylpyrrolidone and styrene (sold by GAF Corp.; dried before use.) |
| PLP = | poly-L-proline (sold by Sigma Corp.) |
| PLPA = | poly-L-phenylalanine (sold by Sigma Corp.) |

Above experiments 1 to 21 (save for experiment 14) demonstrate that the organic polymer additives encompassed by this invention were very effective in preventing rhodium precipitation from the solutions at 130° C. while the organic monomer additive in experiment 23 was not effective. Experiment 14 appears to indicate that the substitution of a long chain alkyl group on the polar functional amide nitrogen interferes with the ability of the polymer to prevent rhodium loss althrough increasing the amount of polymer (Experiment 15) improved its performance.

EXAMPLE 3

In each experiment, about 20 ml. of a metal complex catalyst precursor solution containing a phosphite ligand as indicated (about 10 mole equivalents of ligand per mole of rhodium) and 250 ppm rhodium as $Rh_4(CO)_{12}$ dissolved in Texanol ® solvent was charged under nitrogen to a nitrogen-flushed three ounce glass aerosol bottle equipped with a magnetic stirring bar. Rhodium black if employed, and either (PVP) polyvinylpyrrolidone (avg. mol. wt. 10,000 PVP K-15, GAF Corp.) or (PVPVA) vinylpyrrolidone-vinylacetate copolymer (60% vinylpyrrolidone, S-630, GAF Corp.) as indicated were then added. A nitrogen-flushed gas manifold was attached to the bottle and the system charged to 60 psig with syn gas ($CO/H_2$, 1:1 mole ratio) and vented five times before a final charging with 60 psig. $CO/H_2$. The bottle was placed in an oil bath at the indicated temperature and stirred for one hour to activate the catalyst, whereupon the $CO/H_2$ was vented and the flask charged to 10 psig. with hydrogen or 60 psig. nitrogen as indicated and vented five times. After a final charge of 10 psig. $H_2$ or 60 psig. nitrogen as indicated the flask was stirred for about 20 hours at the indicated temperature, whereupon a sample was withdrawn by pressure syringe and filtered through a Millipore ® five micron type LS filter (Waters Corp.) and analyzed for rhodium content by atomic absorption spectroscopy. The results are shown in the following table.

TABLE 3

| Run Nos. | Ligand | Organic Polymer Additive | Wt. % Organic Polymer Used | Temp. °C. | Rhodium Black[b] | Gas | % Rhodium Lost |
|---|---|---|---|---|---|---|---|
| 1 | A | PVPVA | 0.1 | 115 | No | $H_2$ | 0 |
| 2 | A | PVPVA | 0.2 | 115 | No | $H_2$ | 0 |
| 3 | A | PVPVA | 0.5 | 115 | No | $H_2$ | 0 |
| 4 | A | PVPVA | 1.0 | 120 | No | $H_2$ | 0 |
| 5 | A | PVPVA | 1.0 | 110 | No | $H_2$ | 0 |
| 6 | A | PVPVA | 1.0 | 130 | No | $H_2$ | 0–3 |
| 7 | A | PVPVA | 1.0 | 140 | No | $H_2$ | 6 |
| 8 | A | PVP | 0.1 | 120 | No | $H_2$ | 4 |
| 9 | A | PVP | 0.2 | 120 | No | $H_2$ | 4 |
| 10 | A | PVP | 0.5 | 120 | No | $H_2$ | 0 |
| 11 | A | PVP | 1.0 | 120 | No | $H_2$ | 0 |
| 12 | A | PVPVA | 1.0 | 120 | Yes | $H_2$ | 0 |
| 13 | E | PVP | 1.0 | 130 | No | $N_2$ | 0 |
| 14 | E | PVP | 1.0 | 120 | Yes | $N_2$ | 0 |
| 15 | E | PVPVA | 1.0 | 130 | Yes | $N_2$ | 0 |
| 16 | F | PVP | 1.0 | 130 | Yes | $N_2$ | 0 |
| 17 | H | PVP | 1.0 | 130 | Yes | $N_2$ | 0 |
| 18 | K | PVP | 1.0 | 130 | Yes | $N_2$ | 28 |
| 19 | I | PVP | 1.0 | 130 | Yes | $N_2$ | 0 |
| 20 | L | PVPVA | 1.0 | 120 | No | $H_2$ | 0 |
| 21 | B | PVPVA | 1.0 | 120 | No | $H_2$ | 3 |

[b]50 mg Rhodium Black when used

The above experiments demonstrate that the PVP and PVPVA organic polymer additives encompassed by this invention were very effective in minimizing or preventing rhodium precipitation from the solutions which employed a variety of diorganophosphite ligands.

EXAMPLE 4

By way of comparision, Example 2 wash repeated, save for employing the following organic additives as indicated in place of those used in Example 2. The results are given in the following table.

TABLE 4

| Run Nos. | Ligand | Organic Polymer Additive | Organic Polymer Additive | % Rhodium Lost |
|---|---|---|---|---|
| 1 | E | None | — | 93 |
| 2 | E | PMMA | 1.0 | 76 |
| 3 | E | PVA | 1.0 | 76 |
| 4 | E | PAN | 1.0 | 95 |
| 5 | E | PS | 1.0 | 90 |
| 6 | E | Gantrez ® ES-225 | 1.0 | 62 |
| 7 | E | Gantrez ® ES-335 | 1.0 | 60 |
| 8 | E | Gantrez ® AN-8194 | 1.0 | 86 |
| 9 | E | PVPY | 1.0 | 91 |

PMMA = polymethylmethacrylate (sold by Aldrich Chem. Co.)
PVA = polyvinylalcohol (sold by Aldrich Chem. Co.)
PAN = polyacrylonitrile (sold by Aldrich Chem. Co.)
PS = polystyrene (sold by Aldrich Chem. Co.)
Gantrez ® ES-225 = monoethylester of methylvinylether maleic anhydride copolymer (sold by GAF Corp.)
Gantrez ® ES-335 = monoisopropyl ester of methylvinylether-maleic anhydride copolymer (sold by GAF Corp.)
Gantrez ® AN-8194 = octadecylvinylether/maleic anhydride copolymer (sold by GAF Corp.)
PVPY = polyvinylpyridine (sold by Aldrich Chem. Co.)

The above experiments demonstrate that the organic polymer additives which are not encompassed by this invention were not effective in preventing rhodium precipitation from the solutions.

EXAMPLE 5

By way of comparison, Run No. 11 shown in Table 3 of Example 3 was repeated wherein of the following indicated organic polymer additives were employed instead of polyvinylpyrrolidone. The results are shown in the following table.

TABLE 5

| Run Nos. | Ligand | Temp. °C. | Organic Polymer Additive | % Rhodium Lost |
|---|---|---|---|---|
| 1 | A | 120 | PS | 41 |
| 2 | A | 120 | PMVE | 70 |

PS = polystyrene (sold by Aldrich Chem. Co.)
PMVE = polymethylvinylether (sold by Aldrich Chem. Co.)

The above experiments demonstrate that the organic polymer additives which are not encompassed by this invention were not effective in preventing rhodium precipitation from the solutions.

EXAMPLE 6

In each experiment, about 20 ml. of a metal complex catalyst precursor solution containing the phosphite ligand referred to herein as Ligand A (about 10 mole equivalents of ligand per mole of rhodium) and different amounts as indicated of rhodium as $Rh_4(CO)_{12}$ dissolved in Texanol ® solvent was charged under nitrogen to a nitrogen-flushed three ounce glass aerosol bottle equipped with a magnetic stirring bar. Rhodium black if employed, and about 1.0 weight percent of either (PVP) polyvinylpyrrolidone (avg. mol. wt 10,000, PVP K-15, GAF Corp.) or (PVPVA) vinylpyrrolidone-vinylacetate copolymer (60% vinylpyrrolidone, S-630, GAF Corp.) were then added. A nitrogen-flushed gas manifold was attached to the bottle and the system charged to 60 psig with syn gas ($CO/H_2$, 1:1 mole ratio) and vented five times before a final charging with 60 psig. $CO/H_2$. The bottle was placed in an oil bath at 120° C. and stirred for one hour to activate the catalyst, whereupon the $CO/H_2$ was vented and the flask charged to 10 psig. with hydrogen and vented five times. After a final charge of 10 psig. $H_2$, the flask was stirred for about 20 hours at 120° C., whereupon a sample was withdrawn by pressure syringe and filtered through a Millipore ® five micron type LS filter (Waters Corp.) and analyzed for rhodium content by atomic absorption spectroscopy. The results are shown in the following table.

TABLE 6

| Run Nos. | Ligand | Organic Polymer Additive | Rhodium (ppm) | % Rhodium Lost |
| --- | --- | --- | --- | --- |
| 1 | A | PVPVA | 500 | 6 |
| 2 | A | PVPVA | 1000 | 3 |
| 3 | A | PVP | 500 | 0 |
| 4 | A | PVP | 1000 | 0 |

The above experiments demonstrate that the organic polymer additives used were effective at preventing rhodium loss at high rhodium concentrations.

EXAMPLE 7

In each experiment, about 20 ml. of a metal complex catalyst precursor solution containing about 1.3 weight percent of the phosphite ligand referred to herein as Ligand A and different amounts as indicated of rhodium as $Rh_4(CO)_{12}$ dissolved in Texanol® solvent was charged under nitrogen to a nitrogen-flushed three ounce glass aerosol bottle equipped with a magnetic stirring bar. The indicated amounts of either (PVP) polyvinylpyrrolidone (avg. mol. wt. 10,000, PVP K-15, GAF Corp.) or (PVPVA) vinylpyrrolidone-vinylacetate copolymer (60% vinylpyrrolidone, S-630 GAF Corp.) were then added. A nitrogen-flushed gas manifold was attached to the bottle and the system charged to 60 psig with syn gas ($CO/H_2$, 1:1 mole ratio) and vented five times before a final charging with 60 psig. $CO/H_2$. The bottle was placed in an oil bath at the indicated temperature and stirred for on hour to activate the catalyst, whereupon the $CO/H_2$ was vented and the flask charged to 10 psig. with hydrogen and vented five times. After a final charge of 10 psig. $H_2$, the flask was stirred for about 20 hours at the indicated temperature, whereupon a sample was withdrawn by pressure syringe and filtered through a Millipore® five micron type LS filter (Waters Corp.) and analyzed for rhodium content by atomic absorption spectroscopy. The results are shown in the following table.

TABLE 7

| Run Nos. | Ligand | Organic Polymer Additive | Wt. % Organic Polymer Used | Rhodium (ppm) | % Rhodium Lost |
| --- | --- | --- | --- | --- | --- |
| 1 | A | PVP | 1.0 | 577 | 0 |
| 2 | A | PVP | 1.0 | 853 | 0 |
| 3 | A | PVP | 1.0 | 1040 | 0 |
| 4 | A | PVPVA | 1.0 | 484 | 0 |
| 5 | A | PVPVA | 1.0 | 717 | 0 |
| 6 | A | PVPVA | 1.0 | 907 | 3 |
| 7 | A | PVPVA | 2.0 | 371 | 0 |
| 8 | A | PVPVA | 2.0 | 634 | 0 |
| 9 | A | PVPVA | 2.0 | 786 | 0 |

The above experiments demonstrate that the organic polymers used were effective at preventing rhodium loss while rhodium concentration was increased as ligand concentration was held constant.

EXAMPLE 8

A continuous hydroformylation of a mixture of butene-1 and butene-2 was carried out for 23 days in the amnner described in Example 10 of U.S. Pat. No. 4,599,206 using a solubilized rhodium-diorganophosphite complex catalyst wherein the diorganophosphite ligand was Ligand E and the vaporizer temperature was 110° C. and some rhodium loss was observed. On day 24 about 0.25 weight percent of polyvinylpyrrolidone (avg. mol. wt. 10,000, PVP K-15, GAF Corp.) was added to reactor 2 as an aqueous solution and no rhodium loss was observed for two days of continuous hydroformylation at the vaporizer temperature of 110° C. Upon raising the vaporizer temperature to 115° C., some rhodium loss was again observed which continued through day 35 of the continuous hydroformylation. On day 36 an additional 0.5 weight percent of the same polyvinylpyrrolidone as an aqueous solution (0.75 wt. % total) was added to reactor 2 and no further rhodium loss was observed for six further days of continuous hydroformylation. Increasing the vaporizer temperature to 125° C. however did produce a loss in rhodium.

EXAMPLE 9

A similar continuous hydroformylation experiment as set forth in Example 10 of U.S. Pat. No. 4,599,206 was carried out using a mixed olefin feed of butene-1 and butene-2 (cis and trans), and 2-t-butyl-4-methoxyphenyl(3,3'-di-t butyl-5,5'-dimethoxy-1, 1'-biphenyl-2,2'diyl]phosph ligand promoter. The start-up and general operating procedures set forth in Example 10 of U.S. Pat. No. 4,599,206 were employed.

The hydroformylation reaction was conducted by charging about 1.03 liters of a catalyst precursor solution of rhodium dicarbonyl acetylacetonate (about 155 ppm rhodium), about 3.4 wt. % 2-t-butyl-4-methoxyphenyl(3,3'-di-t-butyl-5,5'-dimethoxy-1,1'-biphenyl-2,2'diyl]phosphite ligand (about 39.9 mole equivalents of ligand per mole of rhodium), about 1% vinyl pyrrolidone-vinyl acetate copolymer (S-630, 60 percent vinylpyrolidone, sold by GAF Corp.), and about 95.6 wt. % of $C_5$ aldehyde (about 86.2 wt. % valeraldehyde and about 9.4 wt. % valeraldehyde trimer) as solvent to reactor 1. About 1.2 liters of the same catalyst precursor solution was charged to reactor 2.

The hydroformylation reaction conditions as well as the rate of $C_5$ aldehydes produced in gram moles per liter per hour and linear n-valeraldehyde to branched 2-methylbutyraldehyde product ratio over 31 days of continuous hydroformylation is set forth in Table 8 below. The aldehyde was separated from the liquid reaction solution at about 106° to 110° C. and 18–21 psi and no rhodium loss was observed over said 31 days of continuous hydroformylation.

TABLE 8

| Days of Operation | 6.9 | 13.9 | 20.9 | 30.8 |
| --- | --- | --- | --- | --- |
| Butene Feed, mol % | | | | |
| Butene-1 | 5.6 | 5.4 | 5.3 | 5.4 |
| Butene-2 (cis and trans), psia | 94.2 | 91.5 | 91.2 | 90.2 |
| n-Butene | 0.2 | 3.1 | 3.5 | 4.4 |
| Reactor No. 1 | | | | |
| Temperature, °C. | 80.4 | 80.4 | 80.4 | 80.5 |
| Pressure, psia | 185 | 185 | 185 | 185 |
| $H_2$ psia | 65.2 | 68.2 | 61.3 | 65.2 |
| CO, psia | 75.5 | 71.9 | 68.5 | 66.5 |
| Butene-1, psia | 0.5 | 0.4 | 0.4 | 0.4 |
| Butene-2 (cis and trans), psia | 31.1 | 30.0 | 30.9 | 30.3 |
| Reactor No. 2 | | | | |
| Temperature, °C. | 85.0 | 85.0 | 85.3 | 85.4 |
| Pressure, psia | 165 | 165 | 165 | 165 |
| $H_2$, psia | 49.9 | 56.2 | 53.9 | 59.0 |
| CO, psia | 71.9 | 66.5 | 66.6 | 63.7 |
| Butene-1, psia | 0.2 | 0.2 | 0.4 | 0.2 |
| Butene-2 (cis and trans), psia | 14.3 | 12.8 | 12.1 | 12.5 |
| Results | | | | |
| n-Valeraldehyde | 0.40 | 0.38 | 0.38 | 0.37 |

TABLE 8-continued

| Days of Operation | 6.9 | 13.9 | 20.9 | 30.8 |
|---|---|---|---|---|
| 2-Methylbutyraldehyde (g mol/L/hr) | 1.31 | 1.23 | 1.25 | 1.21 |

EXAMPLE 10

A similar continuous hydroformylation experiment as set forth in Example 9 above was carried out using an olefin feed of butene-1, and 2-t-butyl-4-methoxyphenyl(3,3'-di-t-butyl-5,5'-dimethoxy-1,1'-biphenyl-2,2'diyl]phosphite (referred to herein as Ligand A) as the ligand promoter. The start-up and general operating procedures set forth in Example 10 of U.S. Pat. No. 4,599,206 were employed.

The hydroformylation reaction was conducted by charging about 658.5 grams of a catalyst precursor solution of rhodium dicarbonyl acetylacetonate (about 200 ppm rhodium), about 3.7 wt. % 2-t-butyl-4-methoxyphenyl(3,3'-di-t-butyl-5,5'dimethoxy-1,1'-biphenyl-2,2'diyl]phosphite ligand (about 33.7 mole equivalents of ligand per mole of rhodium), about 1% vinyl pyrrolidone-vinyl acetate copolymer (E-735, 70 percent vinylpyrrolidone, sold by GAF Corp.), and about 89.25 wt. % of $C_5$ aldehyde and about 5.0 wt. % of Texanol ®, as solvent to reactor 1. About 752.5 grams of the same catalyst precursor solution was charged to reactor 2.

The average hydroformylation reaction conditions as well as the average rate of $C_5$ aldehydes produced in gram moles per liter per hour and average linear n-valeraldehyde to branched 2-methylbutyraldehyde product ratio over 15 days of continuous hydroformylation is set forth in Table 9 below. The aldehyde was separated from the liquid reaction solution at about 113° C. and 19 psia for days 1-5 and no rhodium loss was observed over said 5 days of continuous hydroformylation. On day 6 the temperature at which the aldehyde was separated from the liquid reaction solution was raised to about 134° C. and maintained there at 29 psia for the remaining 9 days fo continuous hydroformylation. No rhodium loss was obsered over asaid 9 additional days of continuous hydroformylation.

TABLE 9

| Average Operating Conditions Over 15 Days | |
|---|---|
| Butene Feed, mol % | |
| Butene-1 | 99.9 |
| Butene-2 | 0.1 |
| Reactor Nos. 1/2 | |
| Temperature, °C. | 90/90 |
| Pressure, psia | 205/185 |
| $H_2$ psia | 95/90 |
| CO, psia | 74/61 |
| Butene-1, psia | 2.6/0.1 |
| Butene-2 (cis and trans), psia | 10/3 |
| Results | |
| n-Valeraldehyde/ 2-Methylbutyraldehyde ratio | 1.35 to 1 |
| Aldehyde Rate (g mol/L/hr) | 5.7 |

EXAMPLE 11

The continuous hydroformylation experiment of Example 10 above was repeated using the same hydroformylation precursor solution and processing conditions, save for charging about 638.5 grams of the precursor solution to reactor 1 and aobut 725 grams of the same precursor solution to reactor 2. The continuous hydroformylation was carried out for 39 days and the aldehyde product distilled and recovered as indicated below.

The average hydroformylation reaction conditions as well as the average rate of $C_5$ aldehydes produced in gram moles per liter per hour and average linear n-valeraldehyde to branched 2-methylbutyraldehyde product ratio over 34 days of continuous hydroformylation is set forth in Table 10 below. The aldehyde was separated from the liquid reaction solution at about 112° to 114° C. and 17 psia from day 1 to day 25 and at about 120° C. and 17 psia from day 26 to day 29 and no rhodium loss was observed over said 29 days of continuous hydroformylation. The aldehyde was then separated from the liquid reaction solution at about 150° C. and 25 psia from day 30 to day 39 and rhodium loss was observed at a rate of 2 percent per day over said 9 days of continuous hydroformylation.

TABLE 10

| Average Operating Conditions Over 39 Days | |
|---|---|
| Butene Feed, mol % | |
| Butene-1 | 99.9 |
| Butene-2 | 0.1 |
| Reactor Nos. 1/2 | |
| Temperature, °C. | 85/85 |
| Pressure, psia | 207/185 |
| $H_2$ psia | 92/87 |
| CO, psia | 79/70 |
| Butene-1, psia | 4.1/0.1 |
| Butene-2 (cis and trans), psia | 7/3 |
| Results | |
| n-Valeraldehyde/ 2-Methylbutyraldehyde ratio | 1.5 to 1 |
| Aldehyde Rate (g mol/L/hr) | 5.4 |

Various modifications and variations of this invention will be obvious to a worker skilled in the art and it is to be understood that such modifications and variations are to be included within the purview of this application and the sprit and scope of the amended claims.

What is claimed is:

1. A method for minimizing or preventing the precipitation of the rhodium of rhodium-phosphite complex catalyst from solution as rhodium metal or rhodium clusters that may occur during a solubilized rhodium-phosphite complex catalyzed, liquid recycle hydroformulation process for producing aldehyde by reacting an olefinic unsaturated compound with carbon monoxide and hydrogen and which involves the recovery of the aldehyde product by distillation from a reaction product solution containing the solubilized rhodium-phosphite complex catalyst and aldehyde product at a distillation temperature in the range of about 50° C. to about 140° C., said method comprising carrying out said distillation of the aldehyde product from a reaction product solution containing the solubilized rhodium-phosphite complex catalyst, aldehyde product, and in addition an organic polymer containing at least three polar functional amide radicals.

2. A process as defined in claim 1, wherein the amount of the organic polymer additive employed is in the range of about 0.1 to about 5.0 weight percent based on the total weight of the reaction product solution to be distilled.

3. A process as defined in claim 2, wherein the amount of the organic polymer additive employed is in the range of about 0.3 to about 3.0 weight percent based on the total weight of the reaction product solution to be distilled.

4. A process as defined in claim 2, wherein the organic polymer is a polyvinylpyrrolidone or a copolymer containing vinylpyrrolidone.

5. A process as defined in claim 3, wherein the organic polymer is a vinylpyrrolidone-vinyl acetate copolymer.

6. A process as defined in claim 1, wherein said organic polymer is also present in the hydroformyaltion reaction medium and throughout the entire liquid recycle hydroformylation process.

* * * * *